United States Patent
Lin et al.

(10) Patent No.: US 7,338,812 B2
(45) Date of Patent: Mar. 4, 2008

(54) BIOCHEMICAL LABELING MATERIALS AND MANUFACTURING METHOD THEREOF

(75) Inventors: Chin-I Lin, Tainan (TW); Kang-Ping Lin, Taoyuan (TW); Yuh-Jiuan Lin, Taipei (TW); Sheng-Ming Shih, Taipei (TW); K Abraham Joseph, Hsinchu (TW); Chao-Kang Chang, Taoyuan (TW)

(73) Assignee: Industrial Technology Research Institute, Hsinchu (TW)

( * ) Notice: Subject to any disclaimer, the term of this patent is extended or adjusted under 35 U.S.C. 154(b) by 512 days.

(21) Appl. No.: 10/600,830

(22) Filed: Jun. 23, 2003

(65) Prior Publication Data

US 2004/0072373 A1 Apr. 15, 2004

(30) Foreign Application Priority Data

Oct. 15, 2002 (TW) .............................. 91123737 A (51) Int. Cl.
 *G01N 33/544* (2006.01)
(52) U.S. Cl. ..................... 436/528; 436/523; 422/68.1; 422/82.01; 422/98
(58) Field of Classification Search .............. 422/68.1, 422/82.01, 98; 435/6, 91.2; 536/22.1, 23.1; 436/523, 528; 424/490, 403
See application file for complete search history.

(56) References Cited

U.S. PATENT DOCUMENTS 6,458,327 B1 * 10/2002 Vossmeyer ................. 422/68.1

OTHER PUBLICATIONS

Perez et al, Molecularly imprinted nanoparticles prepared by core-shell emulsion polymerization, 2000, J App Poly Sc, 77, 1851-1859.*
Spegel et al, A new approach to capillary electrochromatography: Disposable molecularly imprinted nanoparticles, Jul. 2002, American Laboratory, p. 29-30, 32-33.*
Peng et al, Epitaxial growth of highly luminescent CdSe/CdS Core/Shell nanocrystals with photostability and electronic accessibility, 1997, J Am Chem Soc, 119, 7019-7029.*

* cited by examiner

*Primary Examiner*—Long V. Le
*Assistant Examiner*—Nelson Yang
(74) *Attorney, Agent, or Firm*—Sughrue Mion, PLLC (57) ABSTRACT

A biochemical labeling material and manufacturing method thereof. The manufacturing method provides a plurality of nanoparticles, bonding the nanoparticles to template molecules by molecular imprinting, polymerizing the nanoparticles to form a matrix with uniformly-distributed template molecules, finally removing the template molecules from the matrix to reveal a detection group of the matrix, leaving a cavity with specific area.

11 Claims, 6 Drawing Sheets

BIOCHEMICAL LABELING MATERIALS AND MANUFACTURING METHOD THEREOF

BACKGROUND OF THE INVENTION

1. Field of the Invention

The present invention relates to the field of biochemical labeling materials. More particularly, the invention relates to a biochemical labeling material comprising molecularly imprinted nanoparticles.

2. Description of the Related Art

For an eligible biochemical labeling material, two properties are important; selectivity of analytes, and effectiveness of signals produced after biochemical labeling, with resultant ease of detection.

Conventional biochemical labeling materials utilize the unique selectivity of antibody to antigen to enhance effectiveness. For example, peptide and other proteins are used as polyclonal antibodies that select the analyte via adsorption. Fluorescent reagents are applied to produce "labeled" signals in terms of variations of wavelength and intensity of fluorescence.

As nanotechnology develops, semiconductor-nanocrystals are used as fluorescent probes in biochemical labeling materials. Compared to conventional biochemical labeling materials producing weaker, more difficult-to-observe signals, fluorescent probes of semiconductor-nanocrystals, owing to their narrower energy gap, produce stronger signals and more stable fluorescence, adjustable in different situations for different analytes.

Surface functionalization is performed on most semiconductor-nanocrystals prior to usage as biochemical labeling materials. First, II-IV or III-V group semiconductor-particles (single-semiconductor particles or core-shell particles composed of two semiconductors) are reacted with mercaptoacetic acid to form carboxylic groups attached thereon such that the particles become hydrophilic. Then, proteins are attached to the functionalized particles by covalent bonding. Proteins are polyclonal antibodies able to identify the analyte (i.e. antigen). Once the analyte attaches thereon, the quantum effect of nanocrystal particles generates the signals.

Bruchez et al, in Semiconductor-Nanocrystals as Fluorescent Biological Labels (Science 281, 2013 (1998)) modify the third Si layer of CdSe—CdS core-shell semiconductor-nanocrystal particles to be hydrophilic, and then re-modify the Si layer by different functional group to become reactive with biochemical substances. Different modification by Si is performed to increase quantum effect and improve properties. Different core-shell semiconductor-nanocrystal particles were studied, with the main purpose thereof being the fluorescent labeling of mouse fibroblast cells.

Chen et al (Quantum Dot Bioconjugates for Ultrasensitive Nonisotopic Detection, Science 281, 2016 (1998)) study high-fluorescence-semiconductor quantum dot (Zinc Sulfide-capped cadmium selenide) to bond biochemical molecules by covalent bonds and applied to super-high sensitive biochemical labeling materials. Compared to organic dyes, e.g. rhodamine, the intensity of fluorescence increases 20 times, the stability to photobleaching increases 100 times that, but the Spectrum line width is only ⅓ thereof. The manufacturing method thereof uses ZnS-capped CdSe as the quantum dot, modify the surface by mercaptoacetic acid, and bond with proteins by carboxylic groups.

Tan et al (U.S. Pat. No. 6,548,264) manufacture Ag or Cd semiconductor-nanoparticles by microemulsion and react them with silicate to form a layer of silicate, and a silicate layer is modified to bond with proteins, antibody, or antigen.

Mirkin et al (WO Patent 2001073123 ˋ2001051665 ˋ9804740) synthesize nanoparticle-oligonucleotide conjugates to detect nucleic acid by the color change owing to combination thereof.

Ewart et al (WO Patent 9821587) synthesize omit-human IgG-alkaline phosphatase conjugate ZnS:Cu:Aλ capped fluorescent nanoparticles as label materials.

Nanoparticles have thus far been utilized in manufacture of biochemical labeling materials as discussed above, however, the identifying ability of proteins is limited to certain biochemical substrances, and modification of multilayer-nanocrystal particles broadens of Emission Spectrum and instability of photochemical properties.

SUMMARY OF THE INVENTION

Thus, the purpose of the invention is to provide a biochemical labeling material and manufacturing method thereof in which the advantages of using nanoparticles are maintained and selectivity compared to conventional antibody-antigen design is improved, such that the limitation of analytes is relieved and the biochemical labeling material can identify more types of analyte.

To achieve the purpose, the invention applies molecular imprinting on nanoparticles to endow them with unique selectivity to specific species, and expand the applicability to all kinds of chemical compounds, without limitation to biochemical substances. Moreover, modification of nanoparticles is applied to enhance the effectiveness of signals produced after biochemical labeling.

The manufacturing method of biochemical labeling material provided comprises providing a plurality of nanoparticles, bonding the nanoparticles to a template molecule by molecular imprinting, polymerizing the nanoparticles to form a matrix with uniformly-distributed template molecule, and removing the template molecule from the matrix to reveal a detection group of the matrix and leave a cavity with specific area.

The manufacturing method provided can further comprise a surface functionalization treatment of nanoparticles by fluorescent molecule or electron-transfer molecule.

BRIEF DESCRIPTION OF THE DRAWINGS

The following detailed description, given by way of example and not intended to limit the invention solely to the Example described herein, will best be understood in conjunction with the accompanying drawings, in which.

DETAILED DESCRIPTION OF THE INVENTION

The manufacturing method of biochemical labeling material provided comprises providing a plurality of nanoparticles, bonding the nanoparticles to a template molecule by molecular imprinting, polymerizing the nanoparticles to form a matrix with uniformly-distributed template molecule, and removing the template molecule from the matrix to reveal a detection group of the matrix and leave a cavity with specific area.

Figure 1:
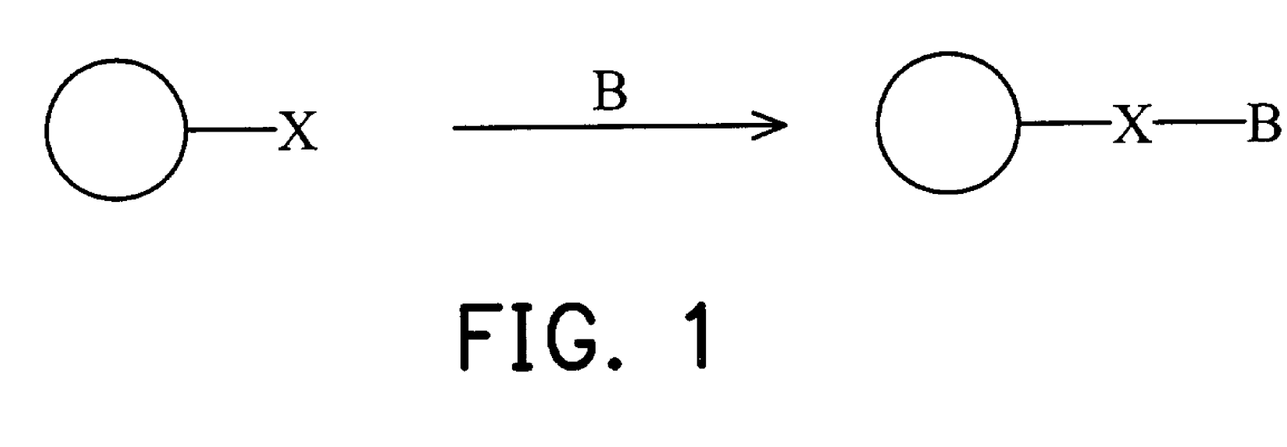
FIG. 1 shows a manufacturing diagram of the present invention.

FIG. 1 shows a manufacturing diagram of the present invention wherein ○ represents a nanoparticle, and B the template molecule, e.g., a bio-organo molecule.

During manufacture, first, a plurality of nanoparticles ○ is provided with an organic-connective molecule x bonded thereon by surface functionalization. Then, molecular imprinting is applied to combine the nanoparticles ○ with template molecules B. In addition, molecular imprinting can also be applied directly on the nanoparticles ○ without advance surface functionalization treatment of nanoparticles.

The nanoparticle ○ in FIG. 1 can be semiconductor-nanoparticle, such as II-VI or III-V group semiconductors as follows.

II-VI: CdS, CdSe, CdTe, ZnS, ZnSe, ZnTe, HgS, HgSe, HgTe or other combinations of duad and quadrivalende; and III-V: InP, GaP, GaInP2, GaAs, InAs, GaN, InN or other combinations of trivalence and pentad.

Nanoparticles applicable in the present invention can also be metal, for example, Au, Ag, Ni, or Co, or metal oxide, for example, $Fe_2O_3$, except semiconductors of II-VI and III-V group and core-shell nanoparticles composed of at least two semiconductors.

Semiconductor-nanoparticles normally illuminate under extra energy due to the band gap thereof usually falling between the spectrum of visible light and infrared, for example, photoluminescence (PL) or electroluminescence (EL). Luminescent properties of the above nanoparticle ○, e.g., intensity or wavelength of luminescence, are related to the reciprocal effect between energy of the organic molecule x and semiconductor-nanoparticle ○, such that when the bio-organo molecule B approaches the nanoparticle ○, the molecular structure of organic molecule x changes, as does the electronic orbit, and thus the reciprocal effect between nanoparticle ○ alters the luminescent intensity and wavelength.

In FIG. 1, organic molecule x performs both energy and electron transfers.

For energy transfer, if x is fluorescent with higher luminant energy than the band gap of semiconductor-nanoparticle ○, x transfers energy to the nanoparticle ○ after excitation to enhance the fluorescent intensity of nanoparticle ○. After connection of x and B results in the yield rate change of fluorescent quantum dots, the fluorescent intensity of semiconductor particle ○ is thereby changed. X can be a fluorescent molecule such as a molecule with resonant structure, electron acceptor, or electron donor, or organic molecule with transition metals or inner-transition metals, such as, dansyl chloride, anthracene, pyrene, coumarine, n-vinylcarbazole, or combination thereof.

If x is an electron-transfer molecule, e.g., an electron donor, x transfers electrons to semiconductor-nanoparticle ○ after excitation to change the fluorescent wavelength of semiconductor-nanoparticle ○. Contrarily, when x is an electron acceptor, electrons are transferred from the semiconductor-nanoparticle ○ to organic molecule x after excitation of x, and the fluorescent wavelength of nanoparticle ○ is changed as well. The electron-transfer ability of x changes if B connects thereon, and the fluorescent wavelength of semiconductor particle ○ changes accordingly. X can be an electron donor, such as amine, porphine molecule with metal for example, Fe or Mn, organic phosphorous molecule. X can also be an electron acceptor, such as fullerene, aromatic, organophosphine, quinone, carotene, or derivatives thereof.

Except for two kinds of x, 3-mercaptopropyl) trimethoxy silane or 3-aminopropyltrimethoxysilane is also applicable to functionalize the surface of nanoparticle to form a functional group capable of forming hydrogen bonding with template molecule. 4-vinyl pyridine and allyl twmercaptothiol are applicable as well to form unsaturated double bonds on the surface nanoparticle. Furthermore, (3-mercaptopropyl) trimethoxy silane and vinyltrimethoxysilane are also applicable to form unsaturated double bonds on the surface nanoparticle.

Molecular imprinting process firstly forms a complex of a template molecule, i.e. bio-organo molecule B in this case, and a monomer by non-covalent or covalent bonds formed therebetween. Polymerization of complexes is then performed under a crosslinking agent, and a biochemical labeling material is finally obtained after removal of template molecule. The interaction between polymer and template molecule is the basis of the high selectivity polymer. The obtained material, as ion exchange resin, has substantially larger apertures and superior hardness. The size of aperture allows permeation of solvents or reagents into the reactive sites to remove the template molecules and bond thereon (if the template molecule is completely surrounded by polymer, the removal is not possible, such that the "reactive site" remains unreactive). The imprinted polymer carries a reactive area having affinity for the target-bio-organo molecule B and acts as the selective absorbent in solid-phase extraction (SPE) and affinity chromatography.

The provided manufacturing method of biochemical labeling material firstly forms a polymer matrix via reaction of surface modified semiconductor-nanoparticles, specific template molecules, functional monomers, initiators, and crosslinking agent. The template molecules are then removed to reveal a detection group of the matrix and leave a cavity with specific area. Nanoparticles as well as molecule-detection groups are thus well distributed in the polymer matrix. The polymer matrix is applicable for a biochemical labeling material due to the quantum effect resulting from the adsorption and desorption of template molecule on nanoparticles.

EXAMPLE 1

The core-shell semiconductor-nanoparticles were prepared as follows. 5 g TOPO was first heated in a flask under vacuum and 190° C. for a few hours, 0.5 ml TOP was then added and the temperature is lowered to 60° C. Then, n-Hexane with about 0.1~0.4 mmol CdSe nanocrystal particles dispersed therein was poured into the reacting flask, and drawn out. The reacting flask with CdSe nanocrystal particles dispersed in TOPO and TOP was further heated and precursors of Zn and S, for example, $ZnEt_2$ and hexamethyl disilathiane respectively, of equivalent molar weight in 2~4 ml TOP were added under nitrogen. The temperature was then lowered to 90° C. after adequate mixing, after continuing mixing for a few hours, CdSe(ZnS) was precipitated by addition of n-butyl alcohol and methyl alcohol.

Figure 2:
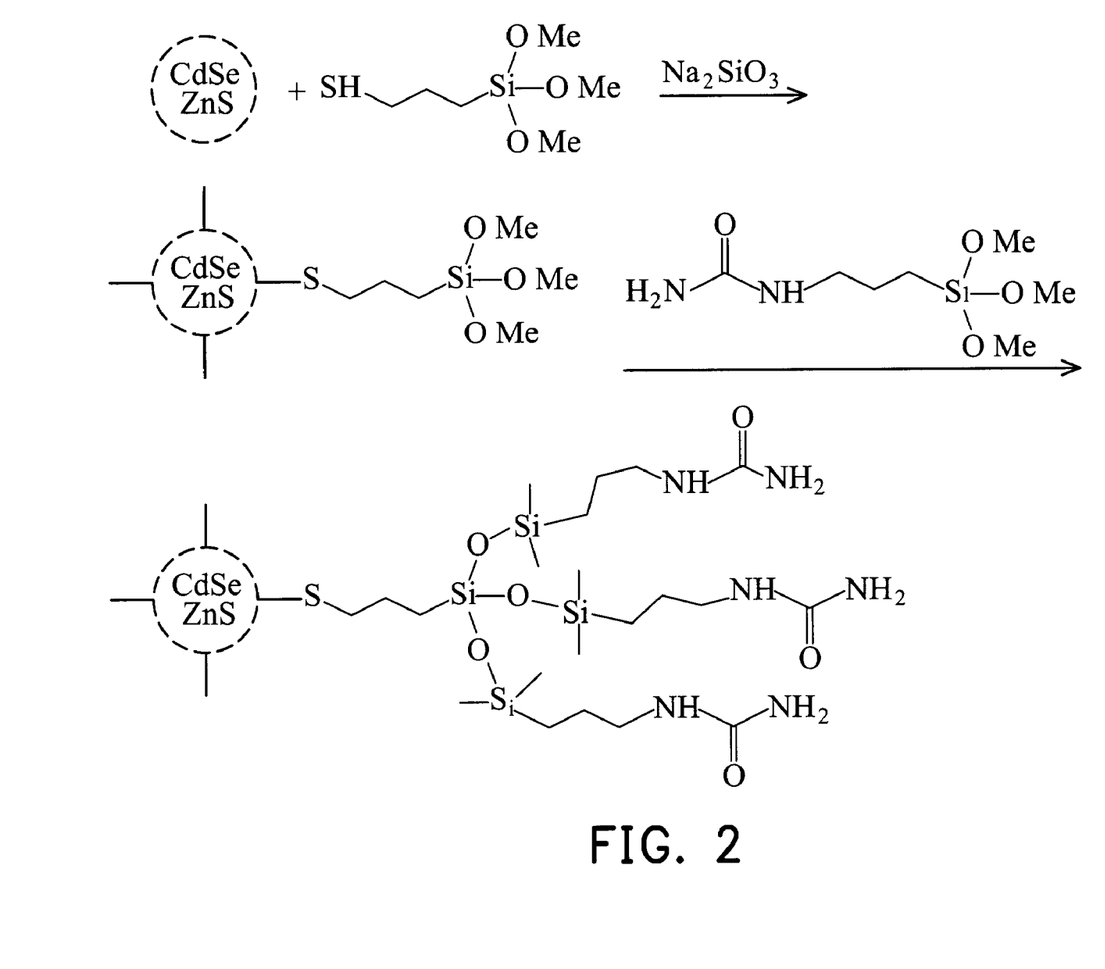
FIG. 2 illustrates surface functionalization of CdSe(ZnS) nanoparticles in the first Example.

In FIG. 2, the surface functionalization of CdSe(ZnS) nanoparticles in the first Example is illustrated.

As in FIG. 2, the surface functionalizaiton of CdSe(ZnS) nanoparticles first dissolves the CdSe(ZnS) nanoparticles in methyl alcohol solvent containing 0.17% (v/v) (3-mercaptopropyl) trimethoxy silane and 25% dimethyl sulfoxide (DMSO) with PH value between 10~11. After overnight mixing, the solution was then diluted with tetramethyl ammonium hydroxide and reflowed at 69° C. for 30 minutes. Then, methyl alcohol solvent containing trimethoxysilylpropyl urea and 3-aminopropyltrimethoxysilane was added after the temperature was lowered, and mixing continued for 2 hours. The solution was reflowed again for 5 minutes and cooled. Basic chlorotrimethylsilane solution was then added and finally 50% acetone, isopropyl alcohol solution was added to precipitate the greasy solid.

EXAMPLE 2

TOP/TOPO capped CdSe nanocrystal particles were first prepared as follows. TOPO was put in a flask to dry under vacuum at 180° C. for 1 hour, and the flask was then filled with nitrogen and heated to 350° C. 1 M TOPSe solution (4 mmole) with $CdSe_2$(2.78 mmole) and TOP (16 ml) were then poured into the stirred TOPO. The particles became mossy after addition of extra methyl alcohol. The mossy precipitate, soluble in organic solvent, was then separated by a centrifuge.

Figure 3:
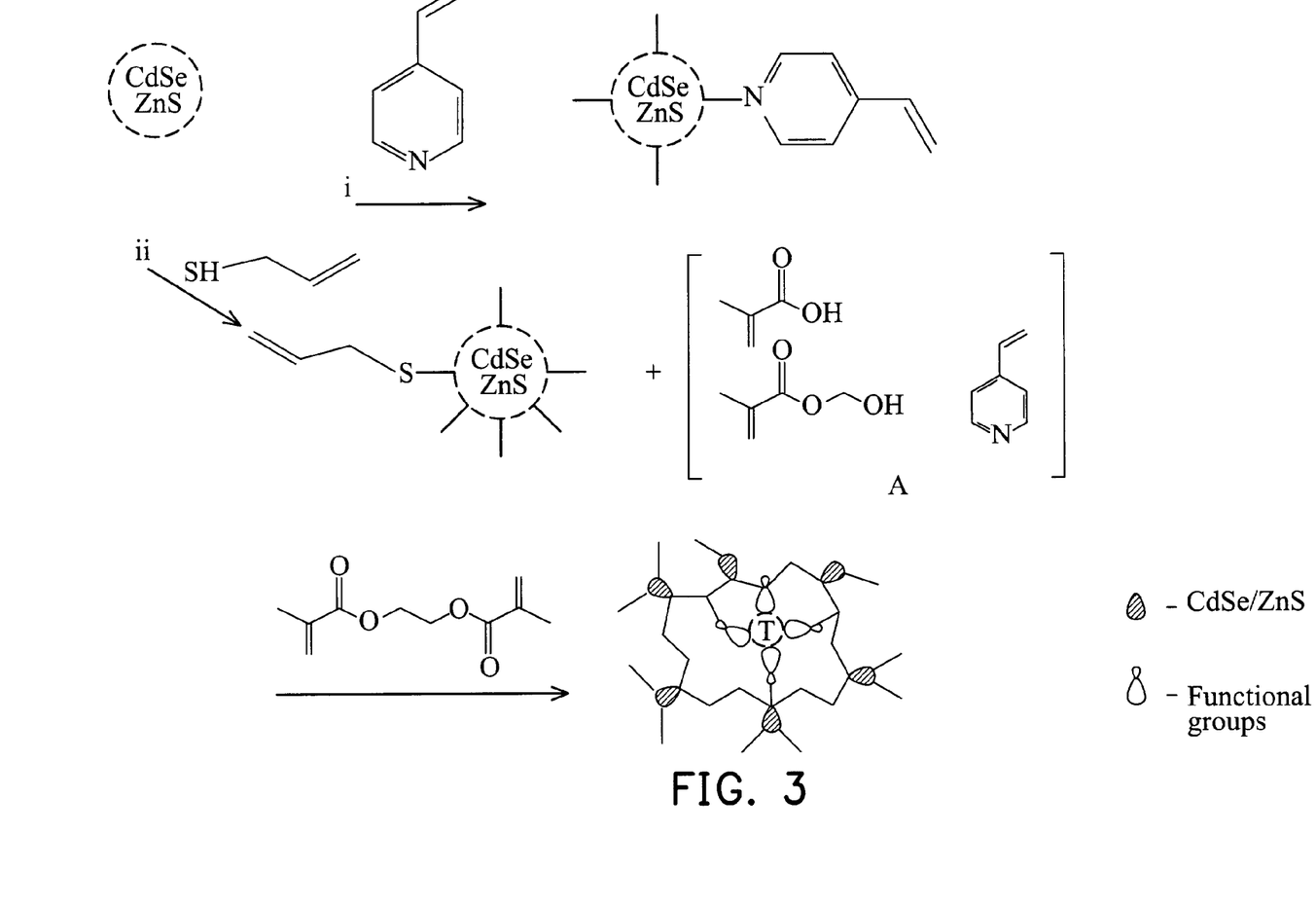
FIG. 3 illustrates manufacture of biochemical labeling material in one Example by covering CdSe(ZnS) nanoparticles with 4-Vinyl pyridine.

As in FIG. 3, nanocrystal particles were first modified as follows.

CdSe(ZnS) was first treated by 4-Vinyl pyridine to perform surface functionalization. The template molecules, such as caffeine, and various functional monomers, such as ethylene glycol dimethacrylate (EGDMA), were then added to form complexes in toluene at 60° C. The initiator, benzoyl peroxide (BPO) was then added to initiate the crosslinking reaction. The polymer matrix with uniformly distributed funtionalized semiconductor nanocrystal particles was obtained after removal of template molecules. The molar ratio of CdSe(ZnS) nanoparticles: caffeine: EGDMA:BPO was 0.8:0.8:140:0.3.

The polymer matrix then underwent the labeling test of the template molecule, caffeine.

Figure 4A:
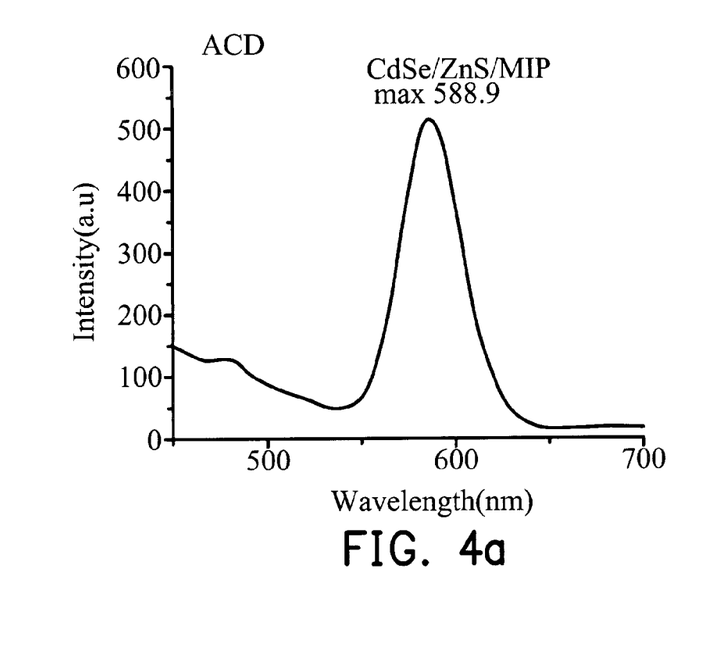
FIG. 4a shows a fluorescent spectrum of polymer matrix of functionalized CdSe(ZnS) nanocrystal particles.
Figure 4B:
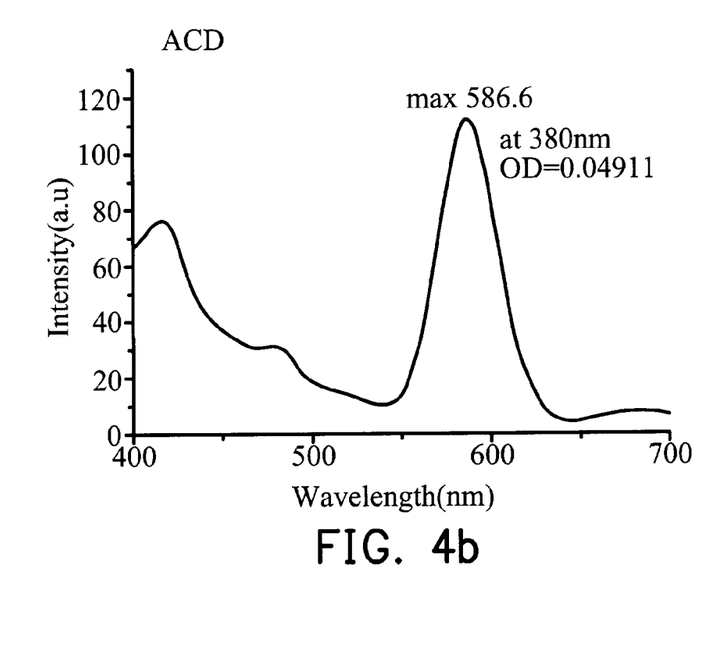
FIG. 4b shows a fluorescent spectrum of caffeine-bonded polymer matrix of functionalized CdSe(ZnS) nanocrystal particles.

FIG. 4a shows a fluorescent spectrum of polymer matrix of functionalized CdSe(ZnS) nanocrystal particles, wherein the maximum intensity is about 520 a.u., indicating the polymer matrix with caffeine molecules bonded thereon brought distinct quantum effect as shown in FIG. 4b in which the fluorescent spectrum of caffeine-bonded polymer matrix of functionalized CdSe(ZnS) nanocrystal particles was displayed, lowering the maximum intensity to about 120 a.u.

Figure 4C:
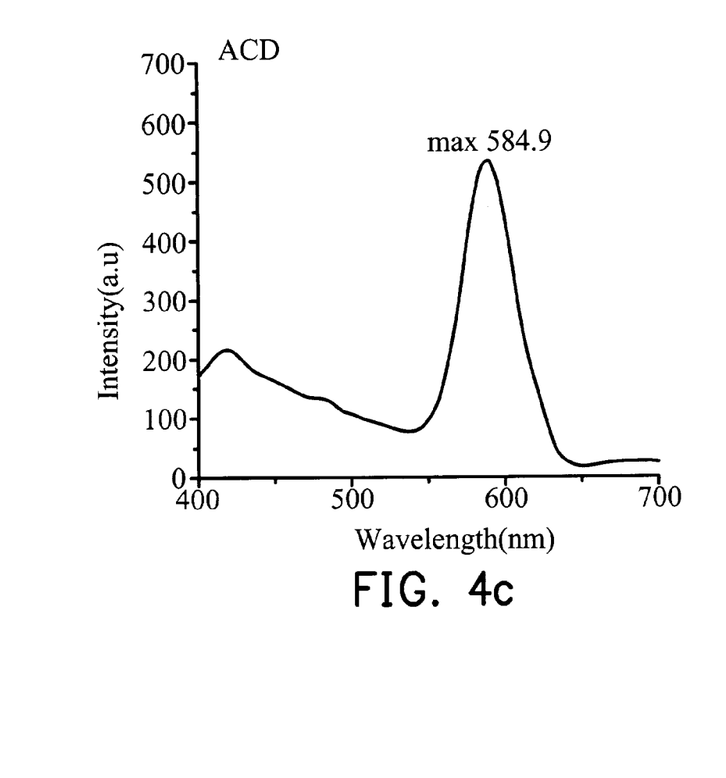
FIG. 4c shows a fluorescent spectrum of polymer matrix of functionalized CdSe(ZnS) nanocrystal particles, after reaction with theobromine.
Figure 4D:
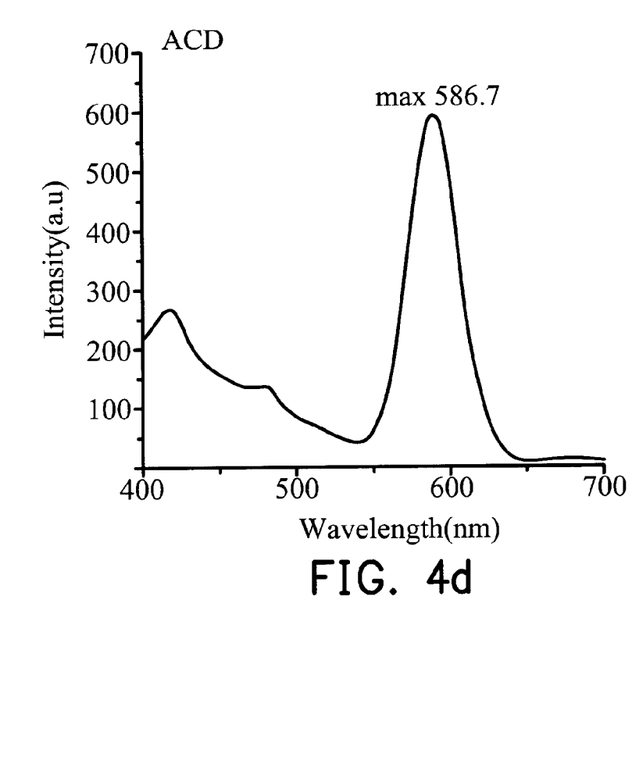
FIG. 4d shows a fluorescent spectrum of polymer matrix of functionalized CdSe(ZnS) nanocrystal particles, after reaction with theophyline.

Molecules with similar molecular structure to caffeine, for example, theobromine and theophyline were then identified by the polymer matrix to test the selectivity thereof. FIG. 4c and FIG. 4d show fluorescent spectrums of polymer matrix of functionalized CdSe(ZnS) nanocrystal particles, after reaction with theobromine and theophyline, respectively. Comparing FIGS. 4c and 4d with 4a, there is no distinct difference, indicating that the polymer matrix did not integrate with theobromine or theophyline, and exhibited detection ability as well as highly specific selectivity to the template molecules of caffeine.

EXAMPLE 3

First, the TOP-TOPO capped CdSe nanocrystal particles were prepared as described in Example 2.

Figure 5:
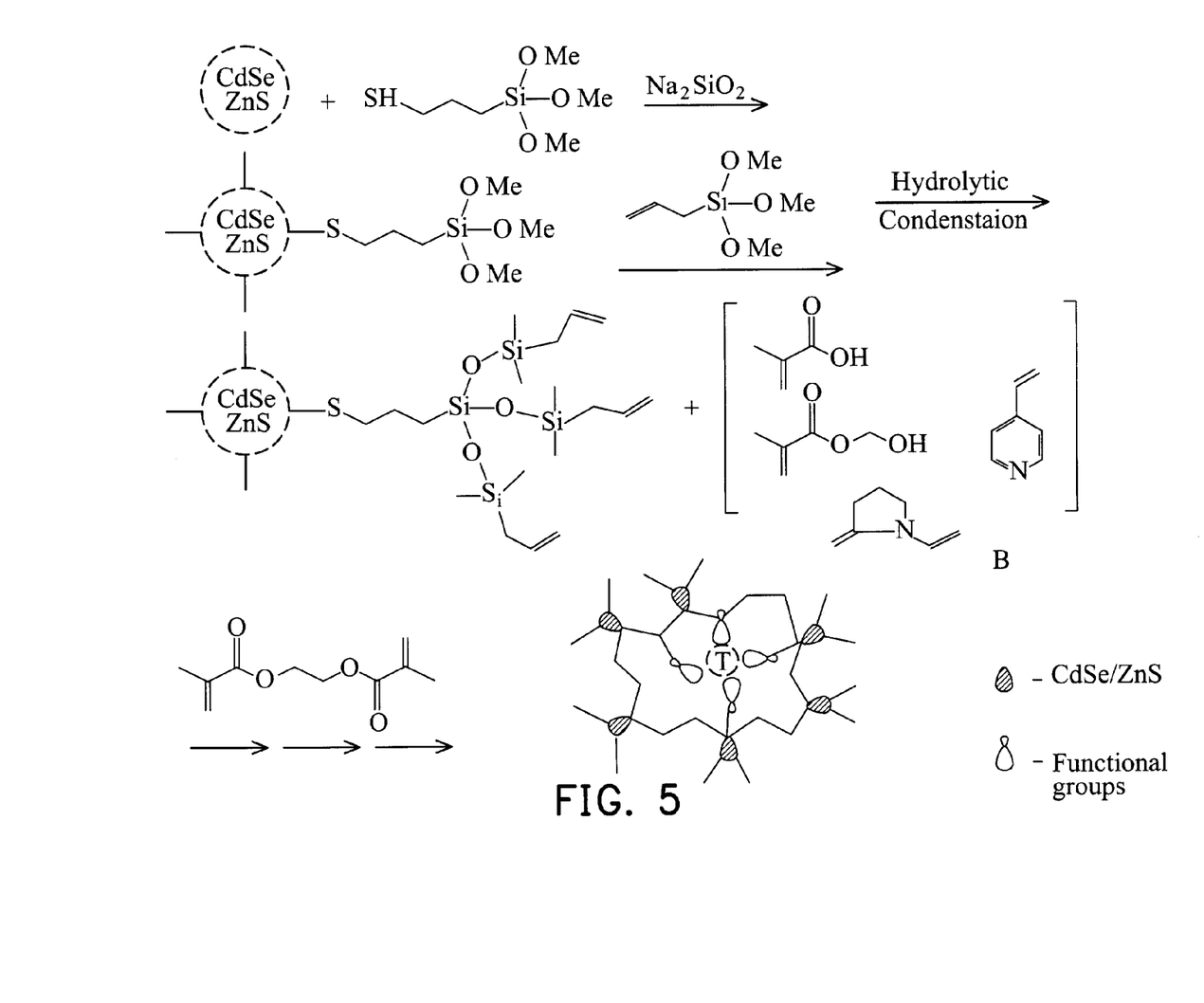
FIG. 5 illustrates manufacture of biochemical labeling material in another more Example by covering CdSe(ZnS) nanoparticles with (3-mercaptopropyl) trimethoxy silane.

As in FIG. 5, the surface functionalization of nanocrystal particles was first performed to bond (3-mercaptopropyl) trimethoxy silane via $Na_2SiO_2$ to CdSe(ZnS), then add vinyltrimethoxysilane and perform hydrolysis concentration reaction with slight acidic catalyst. The reactant obtained forms a polymer matrix with uniformly distributed semiconductor-nanocrystal particles with functional monomers, e.g. EGDMA, a crosslinking agent and template molecules, e.g. caffeine. The molar ratio of CdSe(ZnS): caffeine: EGDMA: catalyst was 0.8:0.8:140:0.3.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A method for manufacturing a biochemical labeling material, comprising:
   providing a plurality of nanoparticles;
   bonding the nanoparticles to template molecules by molecular imprinting, wherein the nanoparticles are semiconductors;
   polymerizing the nanoparticles to form a matrix with uniformly-distributed template molecules, wherein a functional monomer, a crosslinking agent, and an initiator are added during polymerization of the nanoparticles; and
   removing the template molecules from the matrix to leave a cavity with specific area serving as a detection group of the matrix.

2. The method for manufacturing a biochemical labeling material as claimed in claim 1, wherein the nanoparticles are II-VI or III-V group semiconductors.

3. The method for manufacturing a biochemical labeling material as claimed in claim 1, wherein the nanoparticles have core-shell structure of at least two semiconductors.

4. The method for manufacturing a biochemical labeling material as claimed in claim 1, wherein the surface of nanoparticles is further functionalized prior to bonding with template molecules.

5. The method for manufacturing a biochemical labeling material as claimed in claim 4, wherein the surface of nanoparticles is functionalized by fluorescent molecules.

6. The method for manufacturing a biochemical labeling material as claimed in claim 5, wherein the fluorescent molecule is dansyl-chloride, anthracene, pyrene, coumarine, n-vinylcarbazole or derivatives thereof.

7. The method for manufacturing a biochemical labeling material as claimed in claim 4, wherein the surface of nanoparticles is functionalized by electron-transfer molecules.

8. The method for manufacturing a biochemical labeling material as claimed in claim 7, wherein the electron-transfer molecule is amine, porphine, fullerene, organophosphine, carotene or derivatives thereof.

9. The method for manufacturing a biochemical labeling material as claimed in claim 4, wherein the surface of nanoparticles is functionalized by (3-mercaptopropyl) tri methoxy silane or (3-aminopropyl) trimethoxy silane to form a functional group thereon, able to bond to the template molecule by hydrogen bonding.

10. The method for manufacturing a biochemical labeling material as claimed in claim 4, wherein the surface of nanoparticles is functionalized by (4-vinyl pyridine) or allyl mercaptothiol to form an unsaturated double-bond thereon.

11. The method for manufacturing a biochemical labeling material as claimed in claim 4, wherein the surface of nanoparticles is functionalized by (3-mercaptopropyl) trimethoxy silane) or vinyl trimethoxy silane to form an unsaturated double-bond thereon.

* * * * *